(12) United States Patent
Schulhof et al.

(10) Patent No.: US 10,314,673 B2
(45) Date of Patent: *Jun. 11, 2019

(54) SYSTEM FOR PRODUCING A ONE-PIECE ORTHODONTIC JIG AND BRACKETS

(71) Applicant: Orthodontec Inc., Dublin, CA (US)

(72) Inventors: Adam Schulhof, New Milford, NJ (US); Neil Warshawsky, Glenview, IL (US); Sung Kim, San Francisco, CA (US); Leonard Liptak, Dublin, CA (US)

(73) Assignee: Orthodontec Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/726,794

(22) Filed: Jun. 1, 2015

(65) Prior Publication Data

US 2016/0346063 A1 Dec. 1, 2016

(51) Int. Cl.
*A61C 7/00* (2006.01)
*A61C 7/14* (2006.01)

(52) U.S. Cl.
CPC .............. *A61C 7/002* (2013.01); *A61C 7/145* (2013.01); *A61C 7/146* (2013.01)

(58) Field of Classification Search
CPC .......................... A61C 7/002; A61C 7/14–146
See application file for complete search history.

(56) References Cited

U.S. PATENT DOCUMENTS

| | | |
|---|---|---|
| 4,818,226 A | 4/1989 | Berendt et al. |
| 5,100,316 A | 3/1992 | Wildman |
| 5,310,340 A | 5/1994 | Zedda |
| 5,368,478 A | 11/1994 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| 5,882,192 A | 3/1999 | Bergersen |
| 6,988,889 B2 | 1/2006 | Abels et al. |
| 7,077,646 B2 | 7/2006 | Hilliard |
| 7,234,934 B2 | 6/2007 | Rosenberg |
| 7,658,610 B2 | 2/2010 | Knopp |
| 7,811,087 B2 | 10/2010 | Wiechmann et al. |
| 7,950,131 B2 | 5/2011 | Hilliard |
| 8,060,236 B2 | 11/2011 | Hilliard |
| 8,678,817 B2 | 3/2014 | Stevens |
| 8,734,149 B2 | 5/2014 | Phan et al. |

(Continued)

FOREIGN PATENT DOCUMENTS

WO 1994/010935 A1 5/1994

*Primary Examiner* — Eric D. Bertram

(74) *Attorney, Agent, or Firm* — Dorr, Carson & Birney PC

(57) ABSTRACT

A method for producing a one-piece orthodontic jig and brackets employs a computer-aided design (CAD) system to create a model of a patient's dental anatomy. A set of orthodontic brackets and their desired positions are also designed in the CAD model. An orthodontic jig for temporarily positioning the brackets during the bonding process is then designed that includes features for registering the jig to selected teeth, together with connecting members that detachably connect the brackets to the jig and hold the brackets in their desired position on the patient's teeth during the bonding process. The orthodontic jig and brackets is fabricated as a single piece by computer-controlled manufacturing (e.g., 3D printing) based on the CAD model.

11 Claims, 8 Drawing Sheets

(56) References Cited

U.S. PATENT DOCUMENTS

| | | | |
|---|---|---|---|
| 10,028,804 B2 * | 7/2018 | Schulhof | A61C 7/002 |
| 2006/0093982 A1 | 5/2006 | Wen | |
| 2008/0254403 A1 | 10/2008 | Hilliard | |
| 2009/0136890 A1 * | 5/2009 | Kang | A61C 7/145 433/10 |
| 2012/0015315 A1 | 1/2012 | Wiechmann et al. | |
| 2013/0081271 A1 * | 4/2013 | Farzin-Nia | A61C 13/00 29/896.1 |
| 2013/0122445 A1 | 5/2013 | Marston | |
| 2013/0252194 A1 | 9/2013 | Hagelganz et al. | |
| 2013/0323666 A1 | 12/2013 | Vu et al. | |
| 2015/0157421 A1 * | 6/2015 | Martz | A61C 7/08 433/6 |
| 2016/0095670 A1 * | 4/2016 | Witte | A61C 7/146 433/3 |

\* cited by examiner

US 10,314,673 B2

SYSTEM FOR PRODUCING A ONE-PIECE ORTHODONTIC JIG AND BRACKETS

BACKGROUND OF THE INVENTION

Field of the Invention

The present invention relates generally to the field of orthodontics. More specifically, the present invention discloses an automated system for producing a one-piece orthodontic jig and brackets from a CAD model using computer-controlled manufacturing techniques, such as 3D printing.

Statement of the Problem

Orthodontics is the practice of straightening teeth and the harmonizing of the dental occlusion. The orthodontic process typically involves a diagnosis of the patient's pre-treatment dental and occlusal conditions, the development of a treatment plan, and the utilization of medical devices, such as orthodontic braces, to achieve the desired treatment outcome.

Precise bracket positioning, predictable biomechanics, and aesthetics are three orthodontic device performance dimensions that are thought to be critical for achieving efficient and effective treatment outcomes and satisfactory patient experiences. Precise bracket positioning involves placing the brackets on the teeth relative to anatomical landmarks, such as the incisal edge of the teeth, in accordance with the desired prescription. Predictable biomechanics are governed by the ability of the orthodontic bracket to faithfully deliver to the teeth the torque, tip, rotation, in/out, extrusion/intrusion and sliding mechanics movements specified by the prescription. Aesthetics are typically defined as the extent to which the orthodontic devices are invisible and the appliances match the natural shade of the patient's teeth during treatment. Though orthodontists routinely achieve acceptable treatment results with the existing landscape of orthodontic devices, limitations exist. Limitations exist with respect to these three key performance dimensions.

Precise bracket positioning relative to the desired prescription is often beyond the human capability. Placement errors of even a fraction of a millimeter can result in unintended and unpredictable tooth movements. These erroneous tooth movements can lead to unplanned interventions, compensating adjustments, additional appointments, extended treatment times and iatrogenic side effects.

The conventional techniques currently used in orthodontics include direct bonding, in which the practitioner manually positions each bracket on a tooth during the bonding process; and indirect bonding, which uses a bonding tray or placement jig to position a set of brackets on the teeth during bonding. A wide variety of orthodontic bonding trays and placement jigs are commercially available from a number of sources, including Ormco, 3M Unitek, Orapix, American Orthodontics and Orthoselect.

The prior art in this field also includes the following:

U.S. Pat. No. 8,734,149 (Phan et al.) and U.S. Pat. No. 7,658,610 (Knopp) disclose examples of CAD/CAM systems for producing a dental template for etching or for positioning brackets on teeth. However, the brackets are separate objects that must be subsequently placed into the template.

U.S. Pat. Nos. 5,368,478, 5,447,432, 5,454,717 and 5,431,562 (Andreiko et al.) disclose CAD/CAM systems for designing and producing many of the components for conventional orthodontic treatment (i.e., brackets, wires, and jigs), but not as a single piece.

U.S. Pat. Nos. 8,060,236, 7,950,131 and 7,077,646, and U.S. Patent App. Pub. No. 2008/0254403 (Hilliard) disclose examples of CAD/CAM systems for producing orthodontic components, such as orthodontic aligners and archwires.

U.S. Pat. No. 7,234,934 (Rosenberg) discloses a computer-configured orthodontic appliance that incorporates a set of prong units for attachment to selected teeth. A progressive series of computer-configured segmented compartment arches can then be snapped onto the prong units.

It should be noted that all of the above references that employ orthodontic brackets either: (1) require a manual step in positioning the brackets on the teeth, which is time-consuming, subject to errors in bracket order, and inherently introduces a degree of inaccuracy in the position of the brackets on the teeth; or (2) require the user to manually place individual brackets in the correct order into a template or bonding tray, which is also time-consuming and subject to errors in bracket order. In contrast, the present invention is designed to overcome these limitations by providing an automated system that produces an orthodontic jig and brackets as a one-piece directly from a CAD model using computer-controlled manufacturing techniques to address these shortcomings in the prior art.

SUMMARY OF THE INVENTION

This invention provides an automated system for producing a one-piece orthodontic jig and brackets by computer-controlled manufacturing. A computer-aided design (CAD) system is employed to create a model of a patient's dental anatomy, and a set of orthodontic brackets and their desired positions are also designed in the CAD model. An orthodontic jig for temporarily positioning the brackets during the bonding process is then designed that includes features for registering the jig to selected teeth, together with connecting members that detachably connect the brackets to the jig and hold the brackets in their desired position on the patient's teeth during the bonding process. The orthodontic jig and brackets is fabricated as a single piece by computer-controlled manufacturing (e.g., 3D printing) based on the CAD model.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
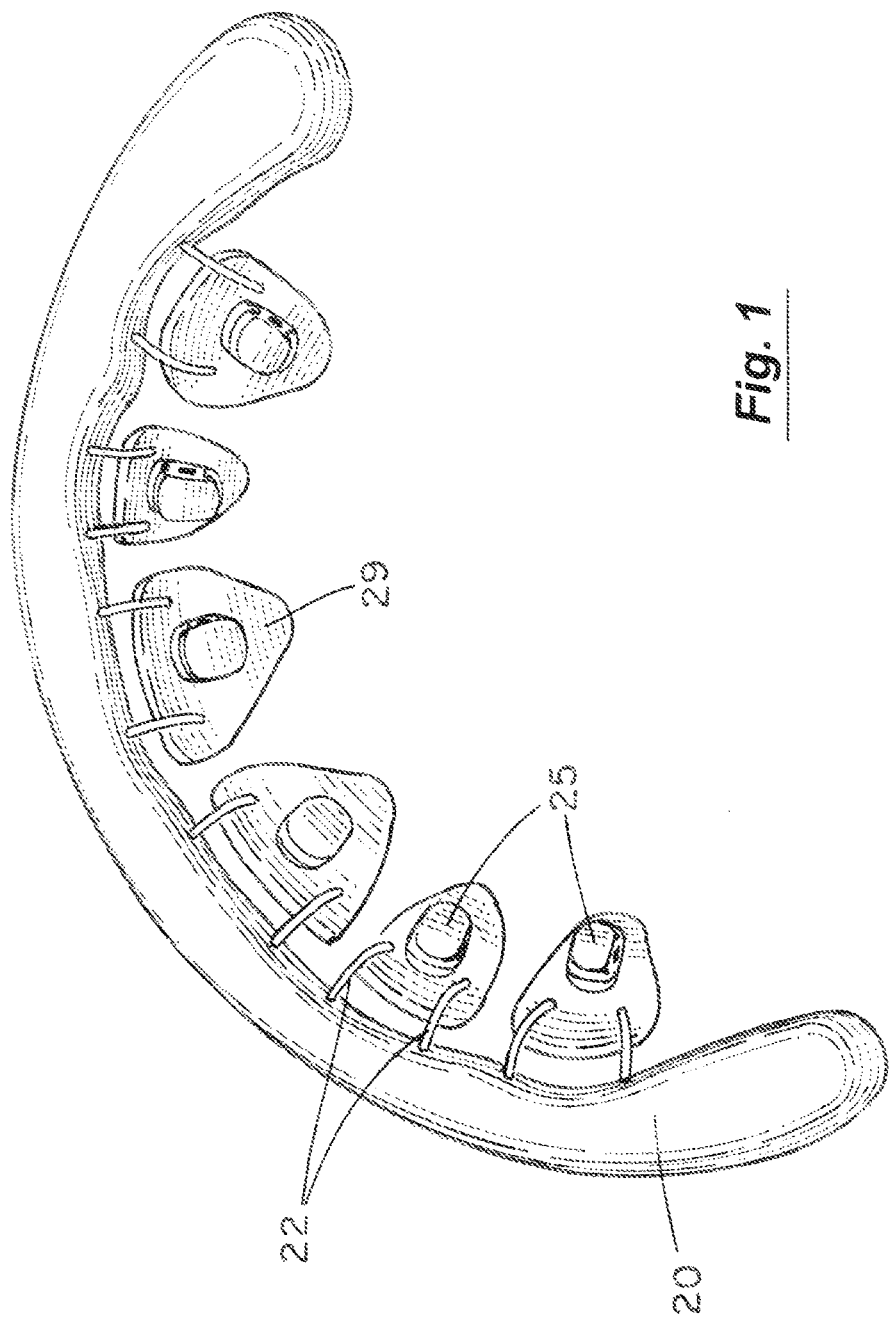
FIG. 1 is a top axonometric view of an example of an orthodontic jig and brackets produced using the present system.
Figure 2:
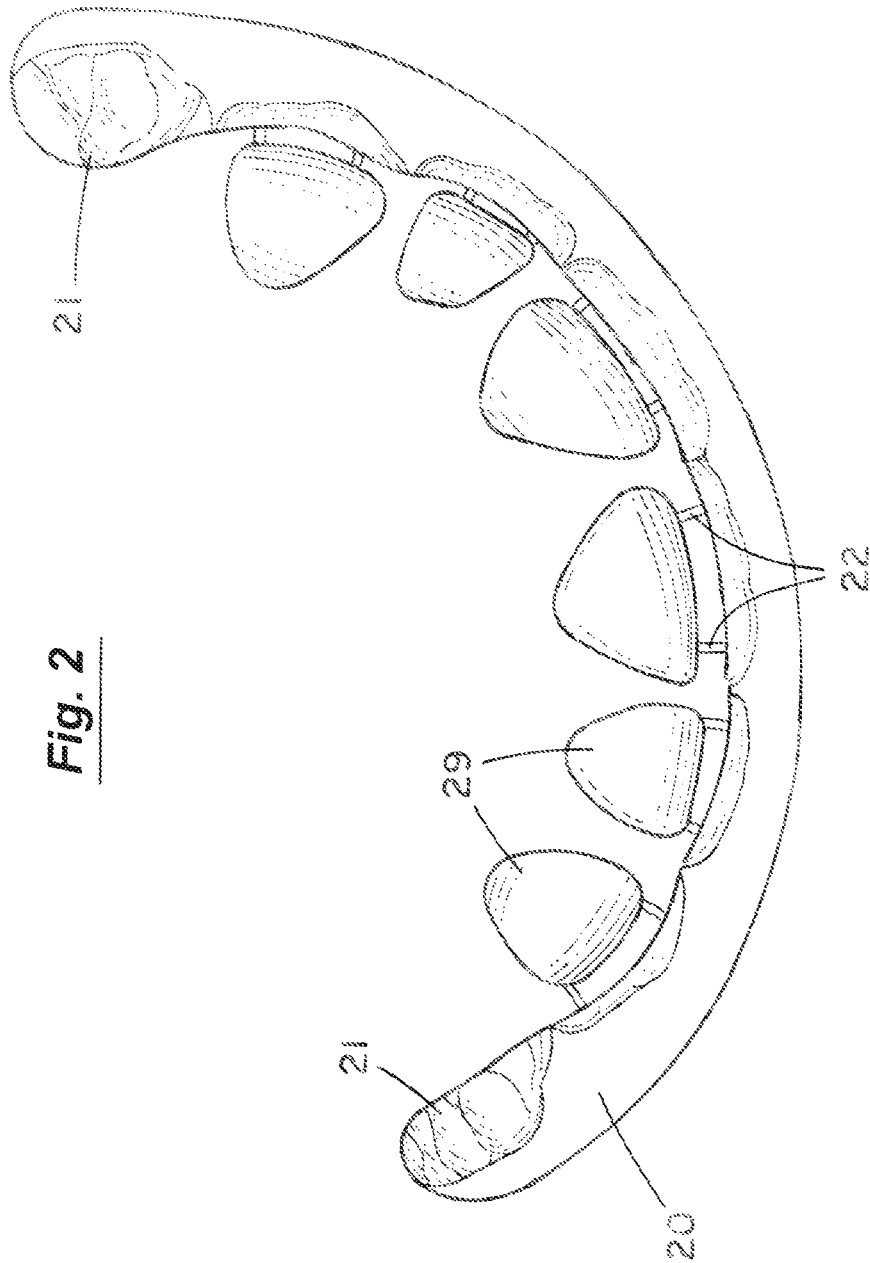
FIG. 2 is a bottom axonometric view of an orthodontic jig and brackets corresponding to FIG. 1.

Turning to FIG. 1, an example is provided of a one-piece orthodontic jig 20 and brackets 25 produced using the present system. FIG. 2 is a corresponding bottom axonometric view. The device includes a patient-specific bracket-positioning jig 20 that typically spans multiple teeth and directly connects to the brackets 25 via a corresponding set of connecting members 22 for the purpose of precise bracket positioning during the bonding process. For example, the bracket locations can be determined from a therapeutic model or a prescription.

Unlike current direct and indirect bracket positioning methods that require the manual step of placing brackets on teeth or on a transfer model for indirect bonding, the present invention is a one-piece system that can be directly manufactured from a patient-specific CAD model using computer-controlled manufacturing techniques, such as 3D printing. Alternatively, the present invention can be used to produce a one-piece model (e.g., a wax or polymer model) by 3D printing that is subsequently used to form a mold for casting the final appliance in a more suitable material, such as metal. The present invention could also be used to directly create a mold for casting the final appliance.

After the appliance has been manufactured, the bracket-positioning jig 20 can be used to precisely position the brackets 25 during the bonding process. In other words, the bracket-positioning jig 20 is designed to directly and precisely transfer the prescribed bracket positioning designed in the CAD system into the actual bracket positioning on a patient's teeth. The connecting members 22 between the bracket-positioning jig 20 and the brackets 25 are designed to be easily detached from the brackets 25 after bonding. The advantage of the one-piece construction is the direct, mechanical transfer of the prescription that eliminates the manual placement of each bracket on each tooth, or transfer model for indirect bonding.

The present device is designed to be utilized across a variety of manufacturing materials as well as common orthodontic bracket design modalities such as slot size and shape, ligation method and bracket design. The components of the present device can be fabricated using a wide range of materials not limited to plastic, metal alloys and ceramics such as zirconia for the purpose of enhancing aesthetics. For example, shaded ceramic and plastic materials allow the device to blend in with the natural color of the patient's teeth.

In the embodiment shown in FIGS. 1 and 2, the bracket-positioning jig 20 is a thin planar member that is curved to generally follow the arch form of a patient's upper or lower dental arch. However, the jig 20 could have other configurations. Here, the jig 20 is designed to rest on the occlusal surfaces of the patient's teeth.

A customized jig mating surface 21 can be formed on the jig 20 at the interface between the occlusal surfaces of the patient's teeth and the jig 20. This jig mating surface 21 can be customized in the CAD process to the teeth of the patient as a direct negative of the occlusal anatomy of the patient's teeth. This creates a positive, unique and tooth-specific match between the occlusal surfaces of the patient's teeth and the jig 20 to help ensure accurate registration of the jig 20 and brackets 25 with respect to the teeth. In turn, this creates a reference point that allows the bracket-positioning prescription to be directly transferred into the positioning of the remaining components of the present device. More generally, other types of features, such as recesses or protrusions, can be included in the design of the jig 20 to help ensure registration of the jig 20 on the patient's teeth during the bonding process.

Figure 6:
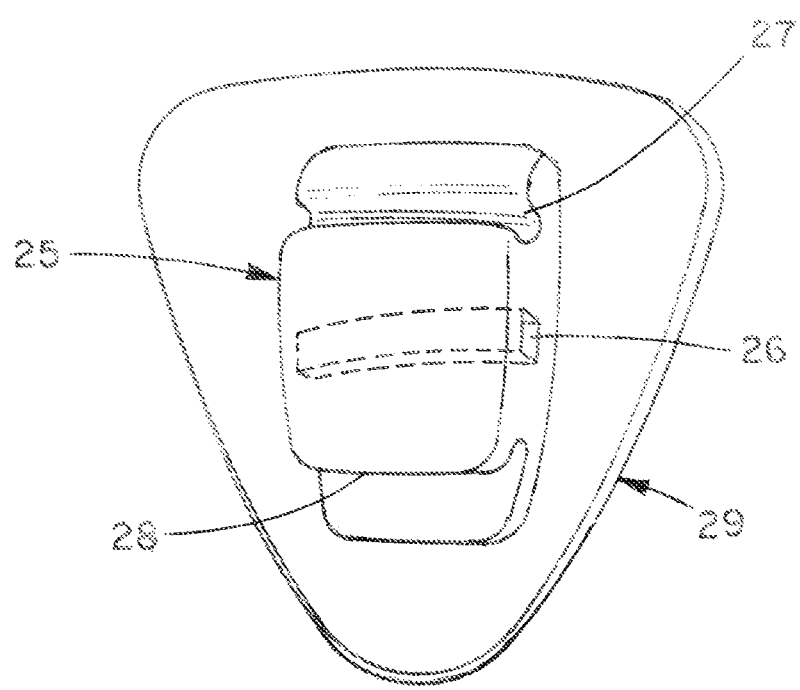
FIG. 6 is an axonometric view of a bracket with a curved archwire slot 26.

The present device also includes a series of orthodontic brackets 25 that feature archwire slots to receive a conventional orthodontic archwire during treatment of the patients. The brackets 25 can be customized during the CAD process to meet specific patient needs and requirements. Each bracket 25 typically includes an archwire slot 26 extending a generally mesial-distal direction, as shown in FIG. 6, that receives and interacts with an archwire during subsequent orthodontic treatment. The cross-sectional shape of the archwire slot 26 may be round, rectangular, square, or other shapes. The brackets 25 can be designed to be placed on the lingual or labial surfaces of the patient's teeth.

Optionally, the brackets 25 can include a patient-specific curved archwire slot 26. FIG. 6 is a front axonometric view of a bracket 25 with a curved archwire slot 26. The curvature, or radius, of the archwire slot 26 can be designed to match the desired arch form prescribed for the patient for the purpose of enhancing the precision and predictability of tooth movement during treatment. For example, the curvature (or radius) of the archwire slot 26 may be based on the arch form prescription for the patient, or a standard preference arch form, or a radius established by the prescribing orthodontist or dentist. Alternatively, the archwire slot 26 can be straight. The archwire slot 26 may also feature a tube-shaped design with enclosures on all sides, or the archwire slot 26 may feature an open slot design with an open side in one dimension, such as the facial or occlusal dimension.

Optionally, the brackets 25 can be equipped with upper or lower auxiliary slots 27, 28 (shown in FIG. 6) to enable the orthodontist to ligate, or hold, an archwire into the archwire slot 25. Placed on the incisal portion of the bracket body relative to the archwire slot 25, the auxiliary slots 27, 28 can also be used as a secondary archwire slot. The auxiliary slots 27, 28 also create a purchase point for the utilization of elastomeric or metal ligatures, power chains, or other auxiliary attachments. The auxiliary slots 27, 28 may be linear or radiused based on the desired arch form for the patient.

Each bracket 25 can also include a custom pad 29 as the interface between the lingual or labial surface of the patient's teeth and the bracket body. The orthodontist typically bonds the bracket to the teeth by applying bonding agents to the pad 29. The mating surface of the pad 29 can be customized during the CAD process to be a direct negative of the dental anatomy of the patient's teeth. The result is a positive, unique, and tooth-specific match between the mating surface of the pad 29 and the labial or lingual surface of the patient's teeth.

Optionally, the brackets 25 can also be equipped with rebonding jig arms that extend from the bracket 25 to allow the orthodontist to precisely position the brackets in the event that the bracket needs to be rebonded or bonded later in treatment. The rebonding jig arms can be customized to match the dental anatomy of each tooth, allowing for accurate bracket positioning.

To summarize, the brackets 25 can be designed during the CAD process in any number of configurations and for multiple ligation methods including, but not limited to metal ligatures, elastomeric ligatures, or self-ligating mechanisms. The present invention is designed for various bracket body, bracket base and tiewing designs including but not limited to twin, edgewise, single wing, Lewis wing, torque in face, torque in base and other designs.

The connecting members 22 are the attachment mechanisms extending from the bracket-positioning jig 20 to each bracket 26. The connecting members 22 are designed to transfer the bracket-positioning prescription for each bracket 25 from the positioning jig 20 to the brackets 25 during the bonding process. After the brackets 25 are bonding, the connecting members 22 are cut, released or detached from the brackets 25 to allow for the removal of the jig 20 after bonding has been completed.

Figure 8:
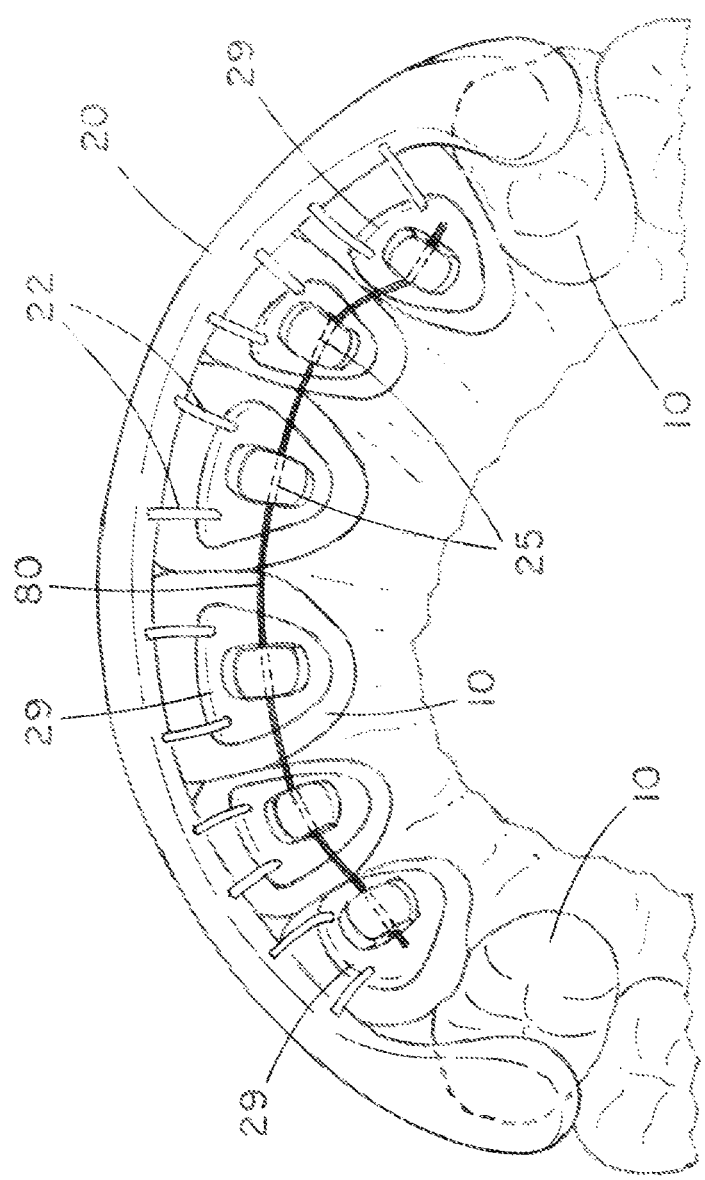
FIG. 8 is a top view similar to FIG. 6 in which a pre-loaded archwire 80 has been added to the brackets 25.

Optionally, a preloaded archwire 80 can be placed into the archwire slots 26 of the brackets 25 (as shown for example in FIG. 8) before the present device is introduced to the patient. The preloaded archwire 80 can be embedded during the fabrication process or inserted at a later time. Preloading the archwire 80 is thought to improve chair time. The archwire 80 can have any of a variety of cross-sectional shapes, including but not limited to round or rectangular; and can be made of any of a variety of materials, including but not limited to nitinol and stainless steel. In this embodiment, the connecting members 22 should be designed with sufficient rigidity to withstand the deflection force of a preloaded archwire 80.

Figure 3:
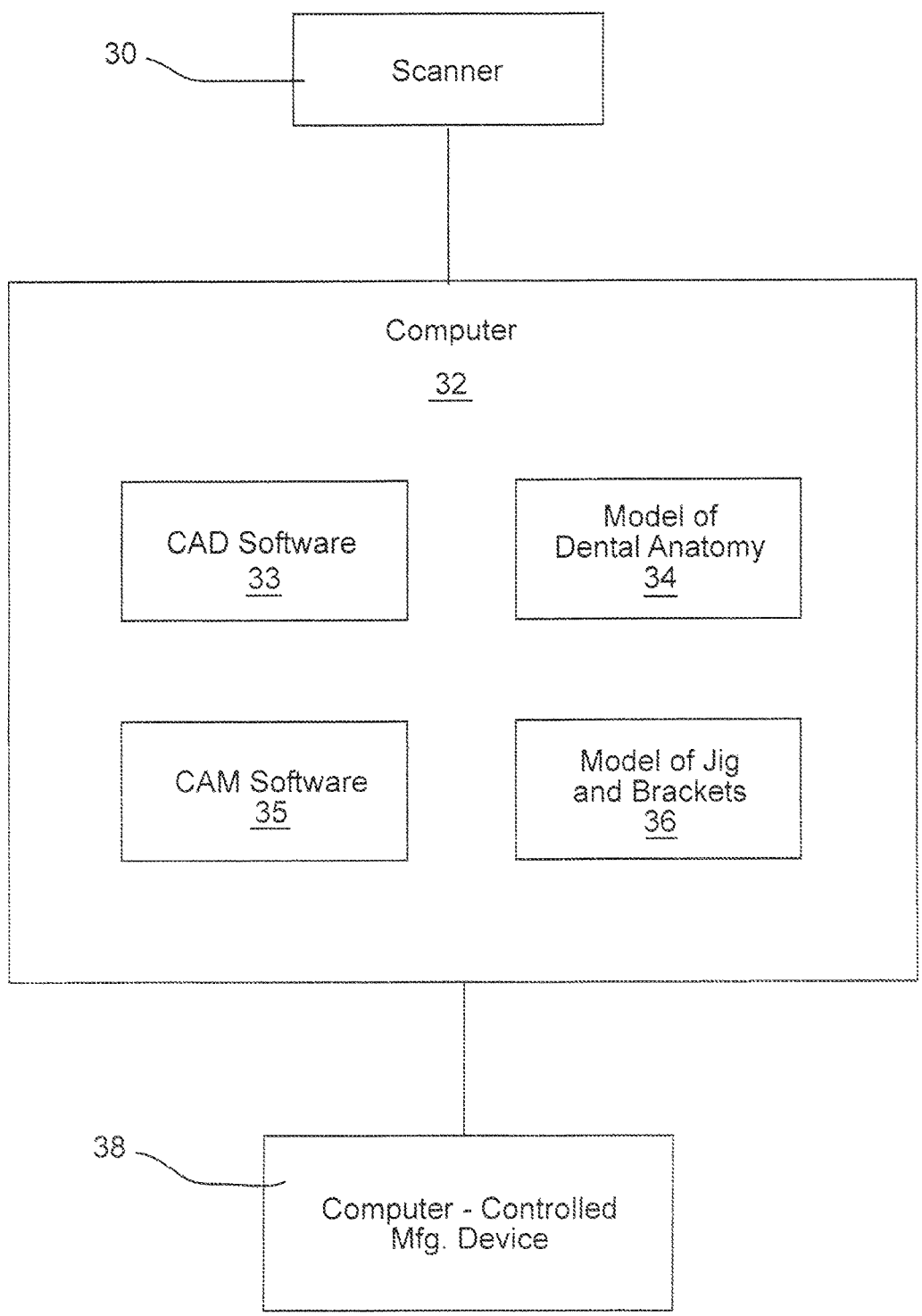
FIG. 3 is a block diagram of the present system.
Figure 4:
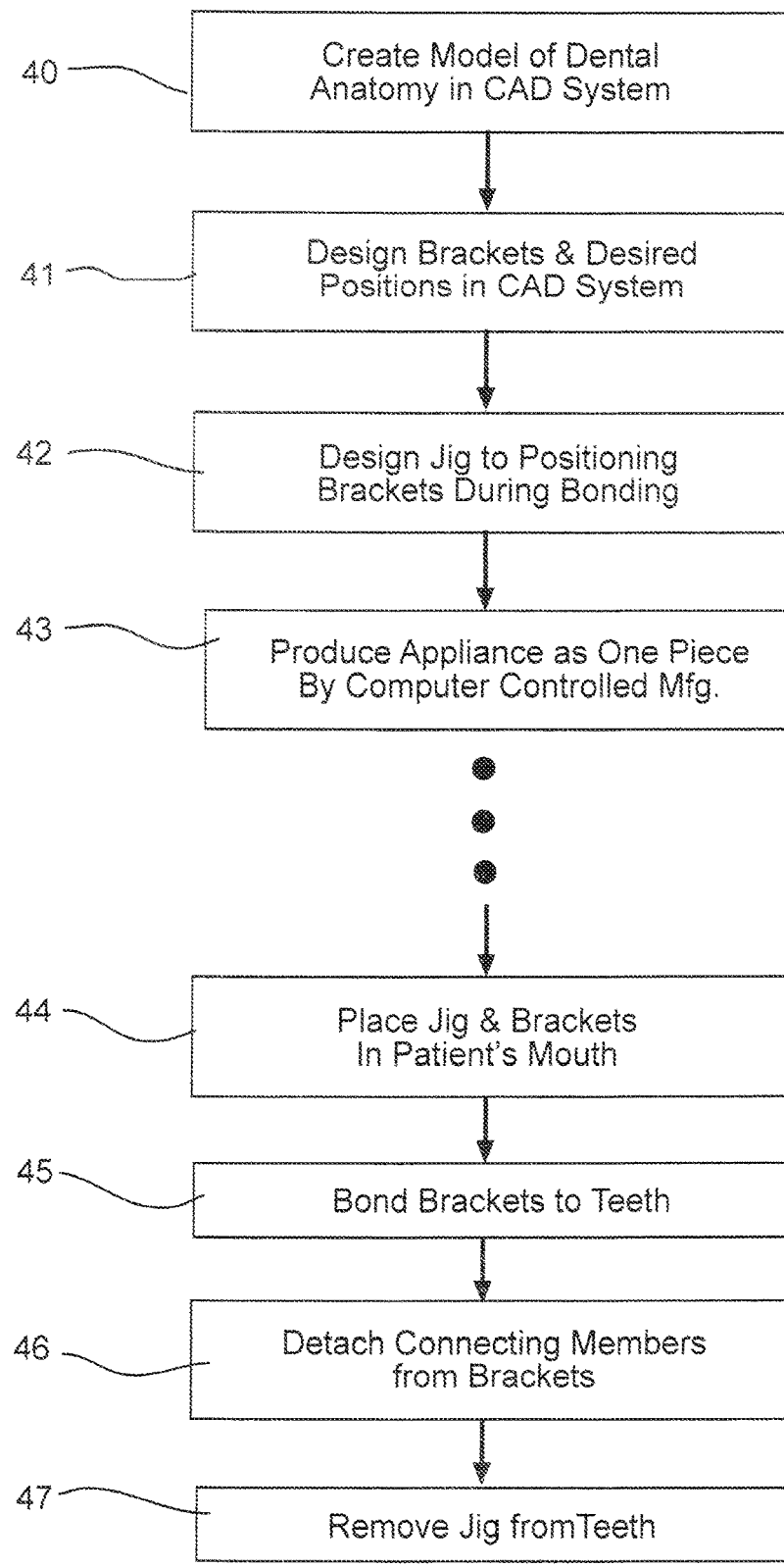
FIG. 4 is a flowchart of the present methodology.

FIG. 3 is a block diagram of an embodiment of the system used to design and fabricate the one-piece orthodontic jig 20 and brackets 25 described above. FIG. 4 is a corresponding flowchart of the steps involved. In step 40, a model 34 of the patient's dental anatomy is initially created using CAD software 33 operating on a conventional computer system 32. For example, the CAD model 34 can be created by optical scanning of the patient's dental anatomy using a scanner 30, as shown in FIG. 3. A scan of conventional stone models of the patient's dental anatomy or dental x-ray imaging could also be employed.

Figure 5:
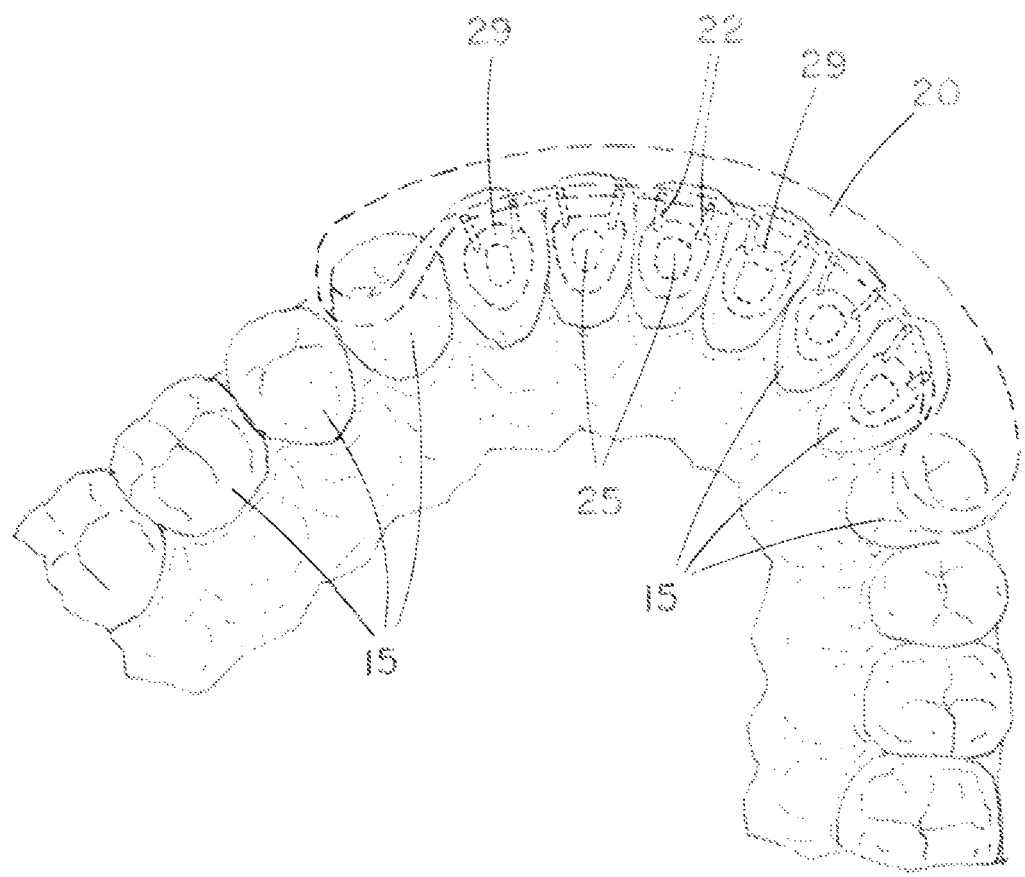
FIG. 5 is a rear axonometric view of a CAD model of a patient's dental anatomy showing the desired placement of orthodontic brackets in dotted lines.

After a CAD model 34 of the patient's dental anatomy has been created, the CAD software 33 can be used by the operator to design a set of orthodontic brackets 25 for treatment of the patient (step 41 in FIG. 4). This typically includes choosing the desired positions of the brackets 25 on selected teeth in the CAD model in accordance with orthodontic practices. As shown for example in FIG. 5, the CAD software 33 enables the operator to interactively view the patient's dental anatomy 15 while designing the placement of the virtual brackets 25. Here, the intended positions of the virtual brackets 25 are illustrated in dotted lines.

In step 42 of FIG. 4, the user continues the design process by creating a CAD model 36 of an orthodontic jig 20 for temporarily positioning the brackets 25 during the bonding process to selected teeth. This jig 20 includes features 21 (e.g., customized mating surfaces) for registering the jig 20 to selected teeth, and also includes connecting members 22 removably connecting the brackets 25 to the jig 20. The connecting members 22 are designed to hold the brackets in their desired positions on the patient's teeth during the subsequent bonding process. The orthodontic jig 20, brackets 25 and connecting members 22 are designed as a single piece, as previously discussed.

In step 43 of FIG. 4, the CAD model 36 of the orthodontic jig 20 and brackets 25 is used by computer-aided manufacturing (CAM) software 35 to generate a set of instructions to control operation of a computer-controlled manufacturing device 38 to produce the orthodontic jig and brackets as a single piece. For example, the appliance can be printed from a suitable polymeric material using a 3D printer, or formed from a blank of a suitable material by CNC milling or machining.

Figure 7:
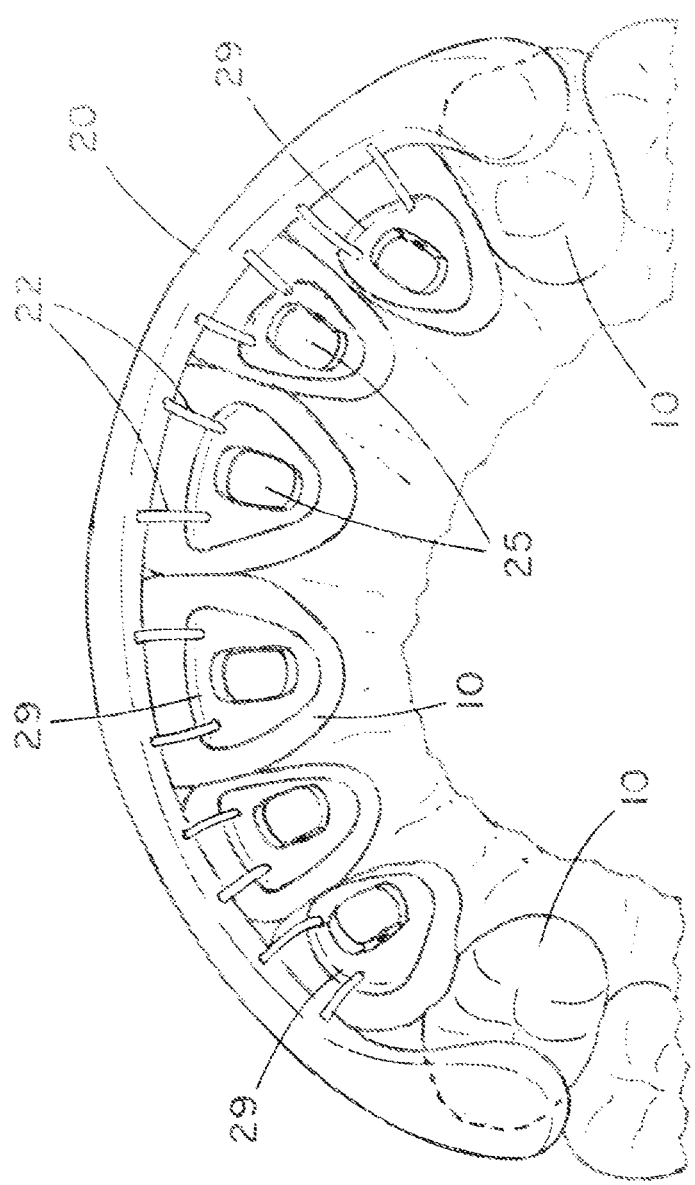
FIG. 7 is a top view of orthodontic jig and brackets in place on a patient's teeth.

After the appliance has been fabricated, it can be placed on the patient's teeth 10, in step 44 of FIG. 4. FIG. 7 is a top view of an example of an orthodontic jig 20 and brackets 25 in place on a patient's teeth 10. The registration features 21 of the orthodontic jig 20 help ensure accurate registration with the teeth 10. In step 45, the brackets 25 are bonded to the patient's teeth 10 with the jig 20 and connecting members 22 providing accurate positioning of the brackets 25 with respect to the teeth 10. Finally, the connecting members 22 are detached from the brackets 25 (step 46) and the orthodontic jig 20 is removed (step 47), while leaving the brackets 25 attached to the patient's teeth 10. For example, the connecting members 22 can be removed by cutting them with small wire cutting pliers or scissors.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A method for producing a one-piece orthodontic jig and brackets comprising:
   creating a model of a patient's dental anatomy in a computer-aided design (CAD) system;
   designing in the CAD model a plurality of orthodontic brackets for treatment of the patient, including the desired positions of the brackets on a selected plurality of teeth in the CAD model;
   designing in the CAD model an orthodontic jig as a single piece with the brackets for temporarily positioning the brackets during the bonding process to selected teeth, said jig including features for registering the jig to the occlusal surfaces of the selected plurality of teeth so that the positions of all of the brackets are fixed with respect to the jig and the selected plurality of teeth, and further including connecting members having thin, elongated members connecting the brackets to the jig designed to hold the brackets in their desired positions on the patient's teeth during the bonding process and that can be cut after bonding to detach the brackets from the jig; and
   producing an orthodontic jig and brackets as a single piece by computer-controlled manufacturing based on the CAD model.

2. The method of claim 1 wherein the orthodontic jig and brackets are produced by three-dimensional printing.

3. The method of claim 1 wherein the orthodontic jig and brackets are produced by computer numerical control (CNC) machining.

4. The method of claim 1 wherein the orthodontic jig and brackets are produced by computer numerical control (CNC) milling.

5. The method of claim 1 wherein at least one of the brackets comprise a curved archwire slot.

6. The one-piece orthodontic jig and brackets made by the process of claim 1.

7. A method of orthodontic treatment comprising:
   creating a model of a patient's dental anatomy in a computer-aided design (CAD) system;
   designing in the CAD model a plurality of orthodontic brackets for treatment of the patient, including the desired positions of the brackets on a selected plurality of teeth in the CAD model;
   designing in the CAD model an orthodontic jig as a single piece with the brackets for temporarily positioning the brackets during the bonding process to selected teeth, said jig including registration features for registering the jig to the occlusal surfaces of the selected plurality of teeth so that the positions of all of the brackets are fixed with respect to the jig and the selected plurality of teeth, and further including connecting members having thin, elongated members connecting the brackets to the jig designed to hold the brackets in their desired position positions on the patient's teeth during the bonding process;

producing an orthodontic jig and brackets as a single piece by computer-controlled manufacturing based on the CAD model;

placing the orthodontic jig and brackets on the patient's teeth using the registration features;

bonding the brackets to the patient's teeth with the jig and connecting members providing accurate positioning of the brackets with respect to the patient's teeth; and cutting the thin, elongated members to detach the brackets and removing the jig from the patient's teeth.

8. The method of claim 7 wherein the orthodontic jig and brackets are produced by three-dimensional printing.

9. The method of claim 7 wherein the orthodontic jig and brackets are produced by computer numerical control (CNC) machining.

10. The method of claim 7 wherein the orthodontic jig and brackets are produced by computer numerical control (CNC) milling.

11. The method of claim 7 wherein at least one of the brackets comprise a curved archwire slot.

* * * * *